United States Patent
Moumene et al.

[11] Patent Number: 5,443,513
[45] Date of Patent: Aug. 22, 1995

[54] COMPOSITE ORTHOPEDIC IMPLANT

[75] Inventors: Missoum Moumene, Teaneck, N.J.; Ruey Y. Lin, New City, N.Y.; Casper F. Stark, Pompton Lakes, N.J.

[73] Assignee: Howmedica Inc., New York, N.Y.

[21] Appl. No.: 171,870

[22] Filed: Dec. 22, 1993

Related U.S. Application Data

[63] Continuation of Ser. No. 855,282, Mar. 23, 1992, abandoned.

[51] Int. Cl.⁶ .................................................. A61F 2/28
[52] U.S. Cl. .......................................... 623/16; 623/23
[58] Field of Search ........................ 623/16, 18, 22, 23

[56] References Cited

U.S. PATENT DOCUMENTS

| | | | |
|---|---|---|---|
| 4,902,297 | 2/1990 | Devanathan | 623/23 |
| 5,180,395 | 1/1993 | Klaue | 623/23 |
| 5,181,930 | 1/1993 | Dumbleton et al. | 623/23 |
| 5,192,330 | 3/1993 | Chang et al. | 623/22 |

FOREIGN PATENT DOCUMENTS

| | | |
|---|---|---|
| 0398064 | 11/1990 | European Pat. Off. |
| 8704916 | 8/1987 | WIPO |
| 9118562 | 12/1991 | WIPO |
| 9218068 | 10/1992 | WIPO |

Primary Examiner—Randall L. Green
Assistant Examiner—Rob Clarke
Attorney, Agent, or Firm—Peter C. Richardson; Lawrence C. Akers; Raymond W. Augustin

[57] ABSTRACT

A beam adapted for implantation within a bone is able to support bending and torsional loading forces applied thereto. The beam has a stiffness defined by a modulus elasticity, which stiffness varies along the length of the beam to match the corresponding stiffness of the cortical bone adjacent the beam after implantation within the bone. The beam is made from an elongated core formed of chopped carbon fibers embedded in a thermoplastic polymer matrix. Encasing the core is a sheath formed of carbon reinforced filament fibers embedded in the thermoplastic polymer which is wound in spiral formation around the core and molded thereto. The winding angle and the sheath thickness along the beam may be varied to vary the modulus of elasticity to match that of the cortical bone adjacent thereto.

15 Claims, 6 Drawing Sheets

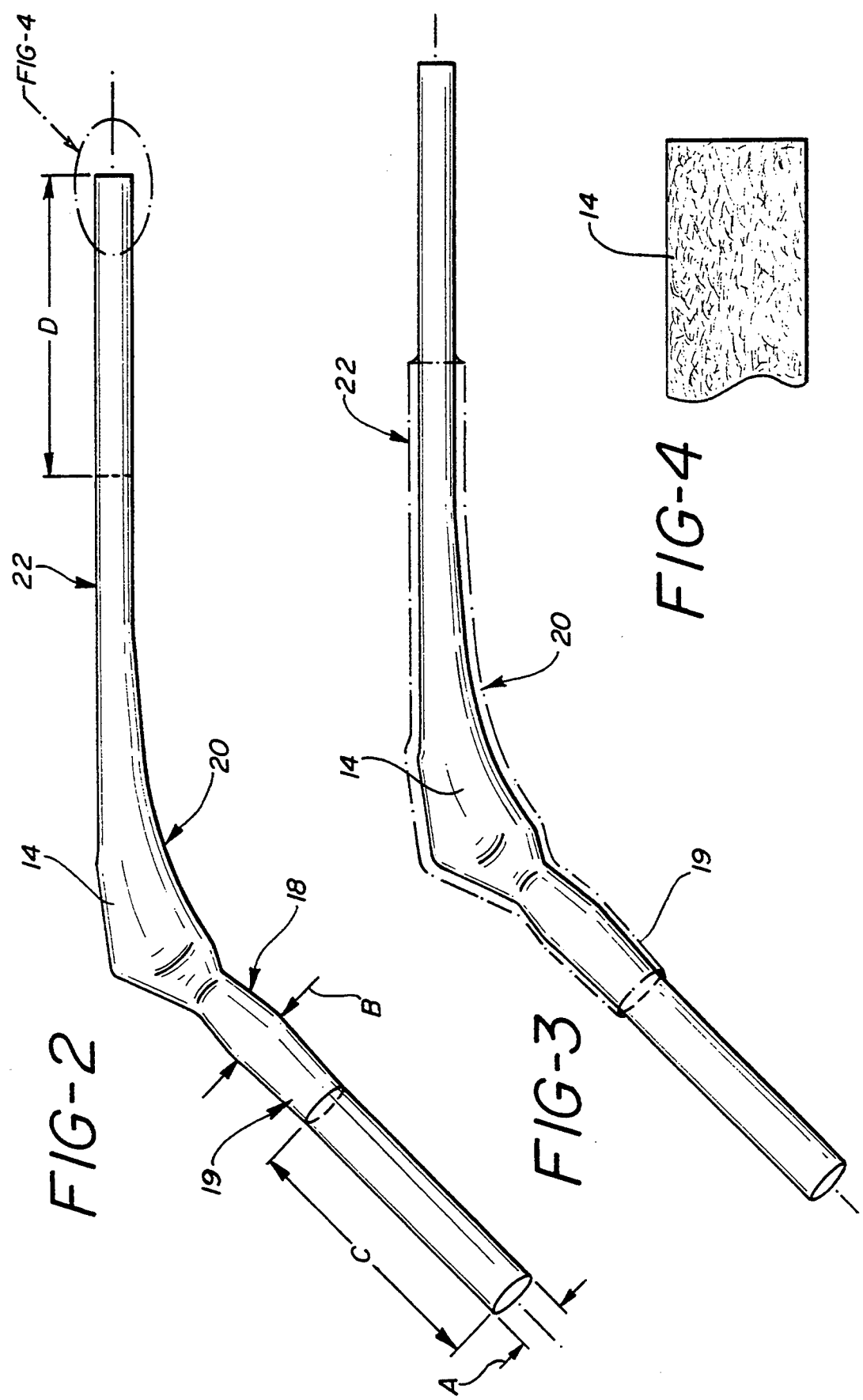

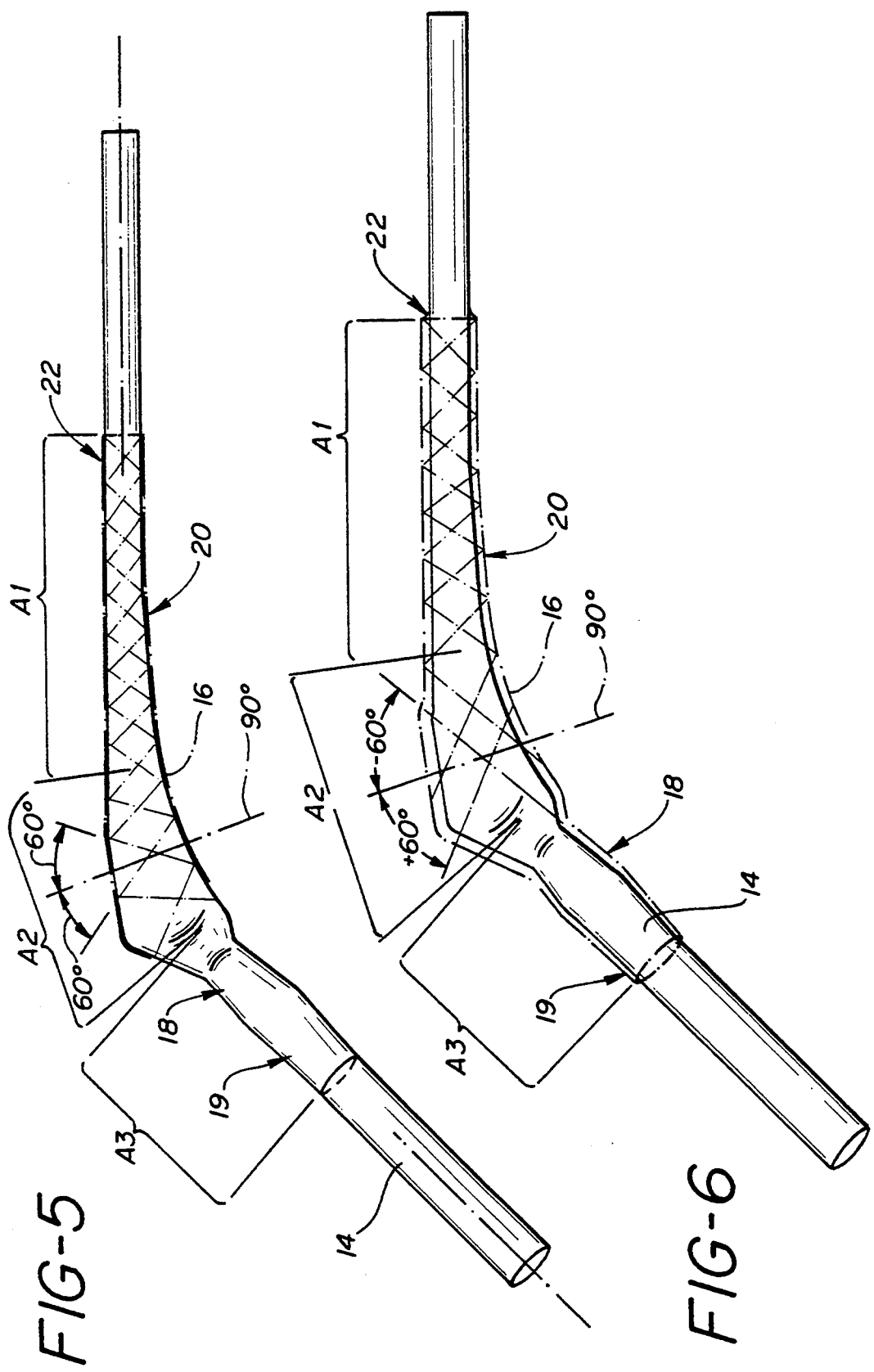

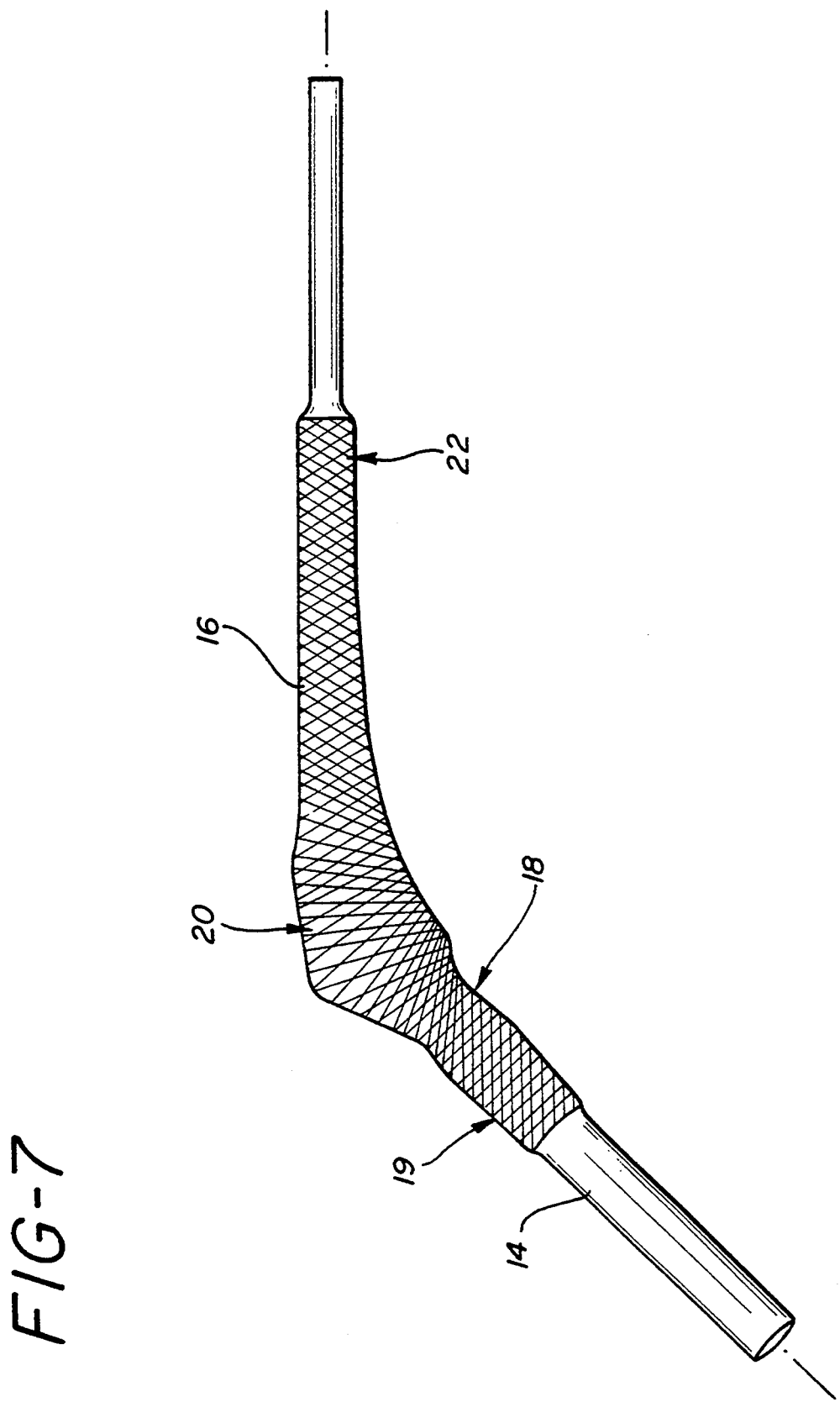

COMPOSITE ORTHOPEDIC IMPLANT

This is a continuation of application Ser. No. 07/855,282, filed on Mar. 23, 1992 now abandoned.

BACKGROUND OF THE INVENTION

1. Field of the Invention

The present invention relates to an improved composite stem construction and method, and particularly, to a composite stem construction for use in a load-bearing joint-replacement prosthetic device.

2. Description of the Prior Art

Stems for orthopedic implants which can withstand both bending and torsion loads are useful in a variety of orthopedic uses. One type of stem which has received considerable attention in the orthopedic field is for a hip joint replacement device. In basic design, this device includes an elongate curved stem which is adapted for receipt in a cavity formed in the proximal region of a femur, and a spherical head carried on a neck at the upper end of the stem. When implanted in operative position, the device functions as a load transfer member between the pelvis and femur, and as such, must accommodate considerable bending, axial compression and torsional forces applied across the joint to the femur.

Various constructions have been proposed previously for hip joint devices of this type. In three of these constructions, the curved stem is adapted for insertion into a bone cavity, and the neck is adapted to support the spherical head, usually via a conical trunion joint. Usually the stem and neck are formed as a single piece, and the spherical head is separately attached to the neck, preferably after inserting the stem into the bone. In one construction the stem and neck are formed as a unitary metal piece from stainless steel or, more preferably, from a cobalt chrome or titanium alloy. An advantage of an all metal construction is that the relatively thick metal stem and neck provide adequate bending and shear strength, so that problems of stem fracture or fatigue are minimal. A disadvantage of the construction is a high degree of stress on certain regions of the bone, and stress protection or shielding in other bone regions. Both high stress and stress shielding can cause bone deterioration and resorption, leading to areas of bone weakness and loss of bone support for the prosthesis.

The related problems of bone stress and stress protection which can occur in a hip joint replacement can be understood from the mechanics of weight load transfer across the hip joint device. Normally, much of the weight load is transferred to the femur near the upper joint region and this load is distributed to and carried by the underlying conical bone region and the prosthesis stem. The distribution of forces in the underlying conical region and prosthesis stem region is determined by the relative stiffness—or elastic modulus—of the bone and stem respectively. In normal bone, the elastic modulus of the outer conical bone region is about $2.5 \times 10^6$ psi, and that of the softer interior cancellous region is less than $1 \times 10^6$ psi, so that weight loading forces are carried primarily by the outer cortical region. By contrast, the metal stem region of a prosthetic device, which replaces the soft cancellous region of bone, has an elastic modulus typically between about $15-35 \times 10^6$ psi, so that much more weight loading is carried by the stem, and much less by the outer cortical bone. In addition to the stress shielding this produces in the bone region adjacent the stem, the high-modulus stem also produces unnaturally high bone stress at the lower or distal tip of the stem, where forces carried in the stem are transmitted to the bone.

In a second known prosthesis construction, the stem and neck are formed from rolled or laminated layers of a composite material containing oriented carbon fibers embedded in a polymer resin. This construction is described generally in U.S. Pat. No. 4,892,552, which issued on Jan. 9, 1990, entitled "Orthopedic Device". In a preferred embodiment described therein, a series of composite layers containing fibers oriented in different directions are laminated, according to known composite block construction methods, to produce a machinable block whose different fiber orientations confer strength in different, selected directions with respect to the long axis of the block. The laminated block is then machined to produce a stem and neck piece which can be implanted in bone and fitted with a ball-like joint member.

Since the laminate structure has a somewhat lower average elastic modulus, both in tension and shear, than a comparable size metal prosthesis, the above problems related to stress protection along the length of the prosthesis stem, and the high concentration of forces at the distal tip of the stem are somewhat reduced. However, the effective elastic moduli of the stem in tension and shear is still very high compared with the soft cancellous region of bone which the stem has replaced. Furthermore, the laminate material is generally not as strong as a comparable size metal stem, particularly at the neck region of the device where weight loading is borne entirely by the prosthesis. This is due in part to the fact that the carbon fibers oriented lengthwise in the stem do not follow the curvature of the stem, and generally do not extend along the entire length of the stem and are not continuous along the stem.

A third prosthesis construction which has been proposed in the prior art involves a metal core having a relatively large-diameter stem which is encased in a low-modulus polymer. A prosthesis of this type is described by Mathis, R., Jr., et al in "Biomechanics: Current Inter-disciplinary Research" (Perren, M., et al, eds.) Martinus Nijhoff, Boston (1985) pp. 371–376. The combined modulus of the polymer and inner core of the device is much more like that of interior cancellous bone than is either a solid metal or laminate composite structure, and as a result, problems related to bone stress protection and high stress are reduced. This compound device has not been entirely satisfactory, however. One problem which has been encountered is fracturing at the neck/stem interface, due to large loading force applied at this juncture by the neck. A second problem is related to the cutting action of the relatively stiff metal core against the low-modulus polymer, in response to forces exerted on the stem in directions normal to the stem's long axis. Over an extended period, the cutting action can lead to core wobbling within the bone, and exaggerated movement of the core in response to loading.

In a fourth prior art device which is described in U.S. Pat. No. 4,750,905, which issued on Jun. 14, 1988, an elongate stem is designed to support a load capable of applying both bending and torsional load forces. The stem generally includes an elongate composite core formed of continuous-filament fibers oriented substantially along the length of the core and embedded in a polymer matrix. Where the core has a curved stem, such as in a hip joint replacement device, the fibers extend in a substantially uniform-density, non-distorted configuration from one end of the core to the other. The core is characterized by high tensile strength and elastic modulus, but relatively low shear strength and modulus.

The core is encased in a sheath which encases the stem and tapered section of the core, but not its upper neck. The sheath is made of braided or woven filaments which encircle the stem in a helical pattern extending along the encased portion of the core. The sheath filaments are bonded to the core by a thermoplastic polymer which is infused into the sheath and heat fused to the core. The polymer which embeds and bonds the sheath to the core is part of a thick polymer skin which forms the shape of the implant which fills the space of a bone cavity in which the device is received.

The problem with this device is that the bending modulus along the stem is fairly constant which can lead to higher than desirable stresses in some localized areas. There has been a need to find a simple way to make the stem stiffer in some areas and more flexible in others.

The implant proposed in copending patent application Ser. No. 07/683,391 assigned to the assignee of the present invention solves this problem by providing a stem with a different elastic modulus at different points along the length of the stem. This is done by placing a reinforcing outer wrap at the surface of the implant and varying the orientation of the reinforcing fibers of the outer wrap along the stem length.

In a circular structural member, it is the outer fibers which are most effective in providing resistance to bending and torsion, and which carry the major portion of the stress in doing so. The role of the outer wrap is to provide the hip prosthesis with the major resistance to bending and torsion required to achieve a design having the desired transfer index and design factor as defined herein-after. The required contribution of the outer wrap to the desired rigidity and strength in each region of the prosthesis is accomplished by varying the orientation of the fibers in the wrap or the thickness of the wrap or both in that region. The outer wrap continues proximally out into the neck region so that joint loads applied to the neck can be transferred rapidly and smoothly to the outer wrap of the prosthesis body without having to be transmitted through the core of the stem below the neck. This is especially important when the outer wrap contacts cortical bone.

The core region of the stem of copending application Ser. No. 07/683,391 consists of unidirectional fibers in a matrix, aligned along the longitudinal axis of the core. The primary function of the core is to provide a strong, stiff neck. The core extends well within the body of the prosthesis in order to securely anchor the neck. The core is used also, although to a lesser degree than the outer wrap, to adjust the rigidity and strength of the body of the prosthesis to achieve the desired stem flexibility.

A filler region is located between the core and the outer wrap and is composed of a material having reduced structural rigidity. This region can act as a mandrel for fabricating the outer wrap. Because the filler contributes little to the overall rigidity of the prosthesis, it permits greater flexibility in adjusting the thickness (number of layers) of the outer wrap to achieve a desired rigidity and strength while maintaining a desired shape. The filler also helps define the shape of the prosthesis for proper fit and transfers stress from the core region to the outer wrap region.

In the present invention the filler has been eliminated and the core has been simplified in construction so that it may be injection molded. The sheath is formed in a similar manner as that of the stem taught in copending application Ser. No. 07/683,391. The construction of the present invention is simpler to manufacture and therefore more economical to produce.

SUMMARY OF THE INVENTION

It is an object of the invention to provide a beam for utilization in an orthopedic implant which has a varying modulus of elasticity along the length thereof which approximates that of the cortical bone adjacent the beam after implantation within a medullary canal.

It is yet another object of the invention to provide a beam which is simple and economical to manufacture and which has properties which can be varied to meet a wide range of applications.

These and other objects of the invention are achieved by a beam adapted for implantation within a bone which is capable of supporting loads applied thereto in bending and torsion. The beam includes an elongated core formed of short chopped fibers embedded in a thermoplastic polymer. These fibers are generally oriented parallel with respect to the longitudinal axis of the beam. A sheath is formed around the core and is composed of carbon reinforced fibers embedded in a thermoplastic matrix, which is then spiral wound around the core and molded thereto. The thermoplastic resin to make the core filler and sheath is polyetheretherketone. The sheath filament fibers are wound around the core at angles with respect to the longitudinal axis of the core which vary along the axis of the core to produce a modulus of elasticity of the beam which varies along the length thereof.

These and other objects and features of the present invention will become apparent from the following detailed description considered in connection with the accompanying drawings, which disclose several embodiments of the invention. It is to be understood that the drawings are to be used for purposes of illustration only, and not as a definition of the limits of the invention.

BRIEF DESCRIPTION OF THE DRAWINGS

In the drawings wherein similar reference characters denote similar elements throughout the several views:

FIG. 2 is a side view of the hip prosthesis core;

FIG. 3 is a view of the core of FIG. 2 showing the wrap in phantom;

FIG. 4 is an enlarged cross-sectional view of the distal stem shown in FIG. 2 showing some parallel alignment of reinforcement short fibers induced by injection molding process;

FIG. 5 is a view of a core of FIG. 2 partially covered in the distal and proximal area by the first sheath layers;

FIG. 6 is a view of the core of FIG. 5 with he final wound sheath outer dimension shown in phantom;

FIG. 7 is a view of the core of FIG. 6 with the outer sheath completely wound thereon;

DETAILED DESCRIPTION OF THE INVENTION

Figure 1:
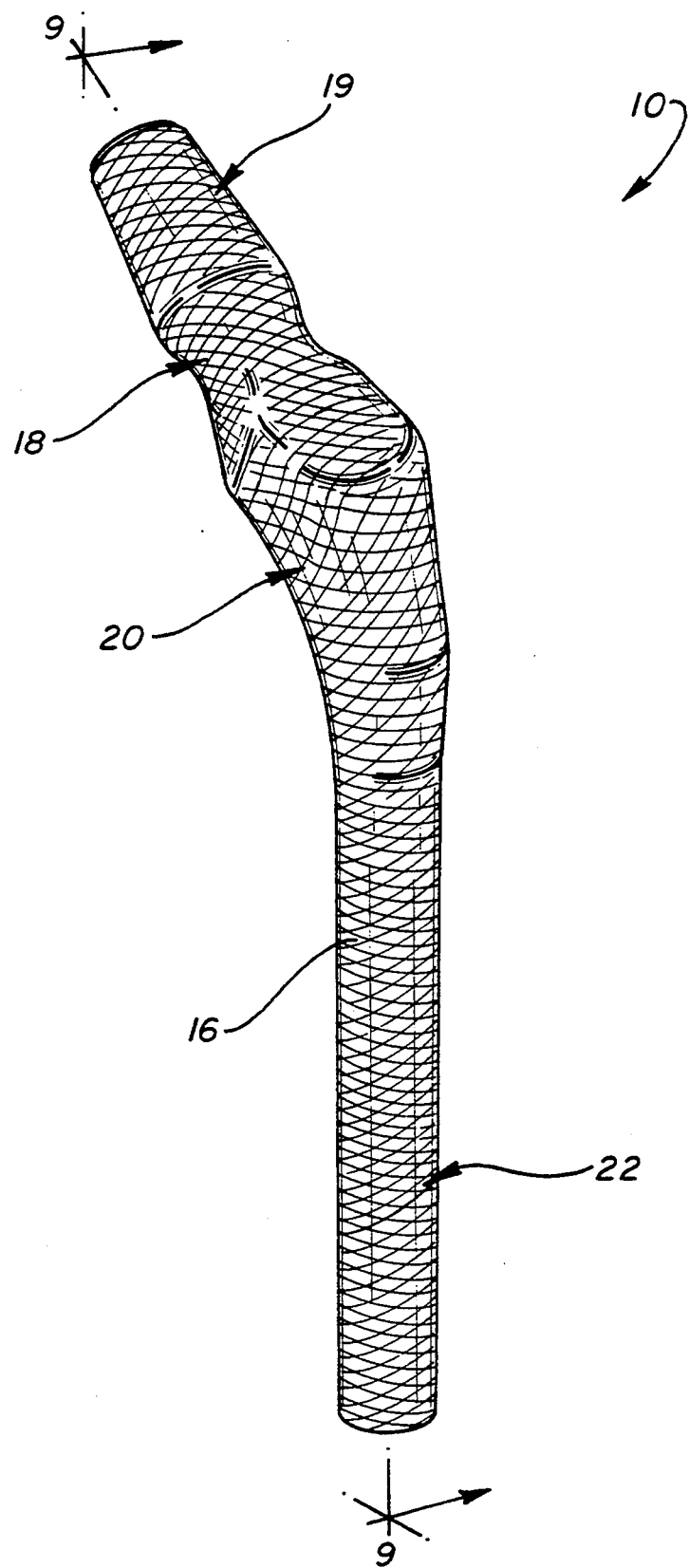
FIG. 1 is an isometric view of a hip prosthesis made in accordance with the present invention.
Figures 8, 9:
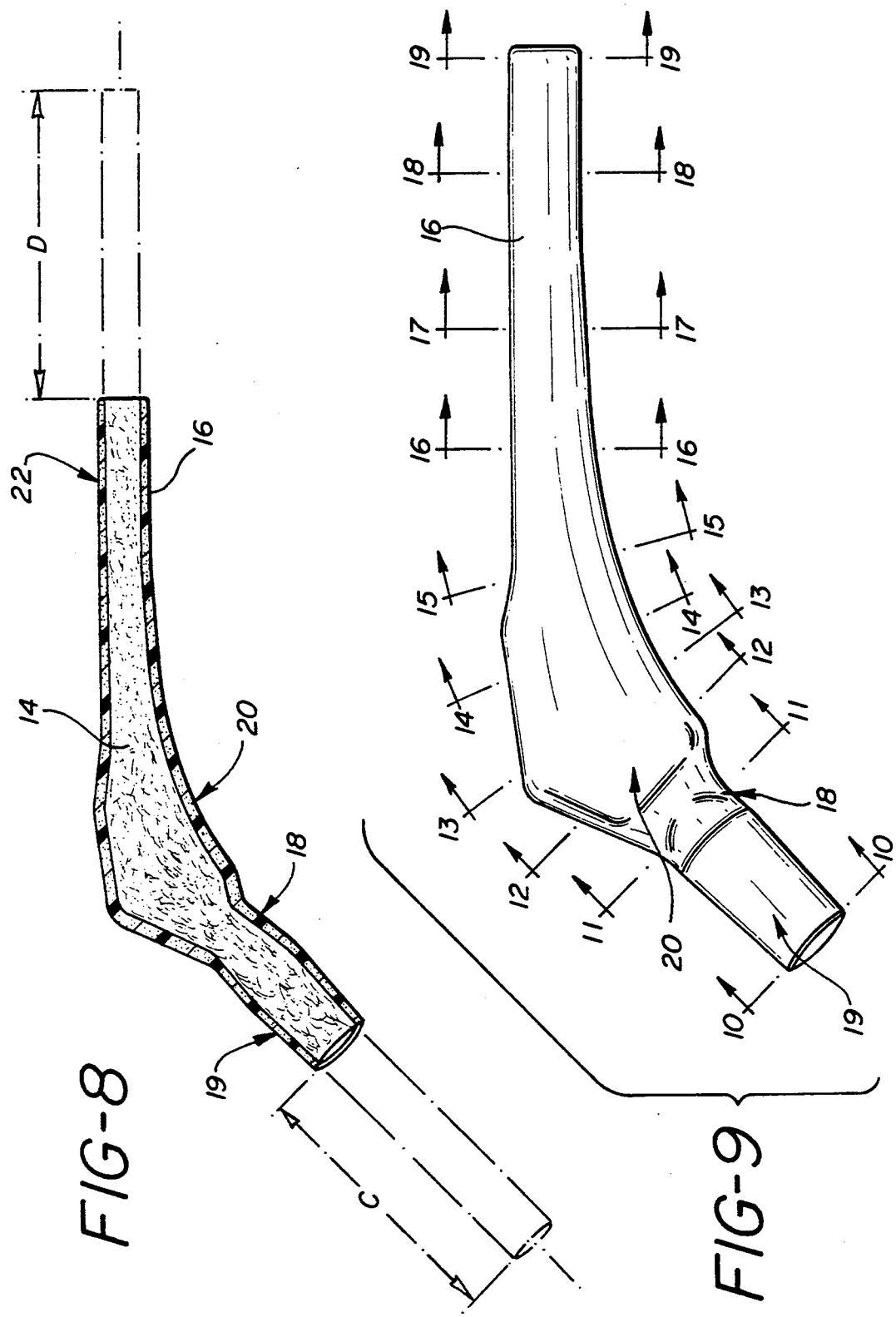
FIG. 8 is a cross-sectional view of the final composite prosthesis with the excess core shown in phantom.
FIG. 9 is a top view of the prosthesis of FIG. 8 after final molding.

Referring to FIGS. 1–8, there is shown the prosthesis of the present invention, generally denoted as 10, which includes a core 14 and an outer wrap or sheath 16. The prosthesis 10 as shown is a hip prosthesis having a neck area 18, a proximal area and a distal area 22. Neck area 18 includes a trunion 19 adapted to receive a spherical head (not shown). While a hip prosthesis is shown, any prosthesis having a stem portion may be made as described herein.

In the preferred embodiment, core 14 extends the entire length of the prosthesis and, in order to provide for holding the prosthesis in a mandrel, may extend a predetermined distance beyond the ends of the desired final length of the prosthetic device. The core 14 not only holds the prosthesis in a mandrel, but it provides bulk material to help achieve the final desired shape of the prosthesis. Furthermore, the core 14 helps in adjusting the stiffness of the prosthesis to accommodate the host bone stiffness by changing the volume ratio of the shod fiber.

Referring to FIGS. 2 and 4, the core is shown to be made of short (2 mm average length, all less than 4 mm) carbon fiber reinforced thermoplastic such as polyetheretherketone (PEEK). In the preferred embodiment, the chopped short fibers make up 20%–40% of the core by volume. The core is injection molded to the shape shown in FIG. 2 which, as stated above, includes sections C and D which extend beyond the desired length of the prosthetic core and are included merely for supporting the core in a mandrel for subsequent processing. Preferential orientation of short carbon fibers along the longitudinal axis of the core are induced by the injection molding process. FIG. 4 shows an enlarged view of the cross-section of the core containing shod fiber reinforcing a thermoplastic resin.

Referring to FIGS. 5–7, there is shown the core 14 wound with a sheath of either carbon fiber reinforced preimpregnated monofilament or preimpregnated carbon fiber reinforced tape of narrow width such as ⅛". This material is wound at angles with respect to the core longitudinal axis, depending on the desired structural modulus along the various sections A1, A2, A3 of the stem. The orientation angles may be varied to match the stiffness of the prosthesis to the precalculated stiffness of, for example, the human femur along the length of the beam or stem.

Referring to FIG. 7 there is shown the final shape of the prosthesis after the core has been wound with, in the preferred embodiment, a sheath or outer wrap containing 12–40 layers of reinforced thermoplastic (prepeg).

Figure 10:
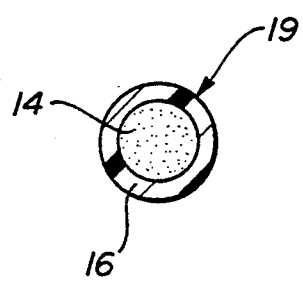
FIG. 10 is a cross-sectional view of the prosthesis of FIG. 9 along line 10—10.
Figure 11:
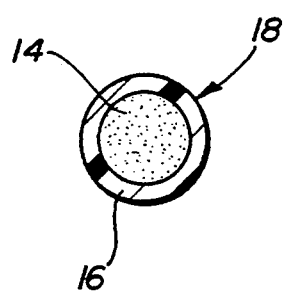
FIG. 11 is a cross-sectional view of the prosthesis of FIG. 9 along line 11—11.
Figure 12:
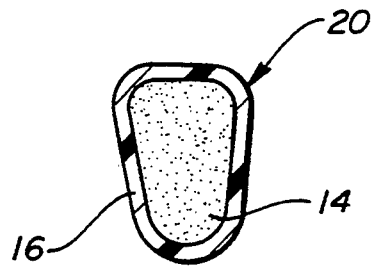
FIG. 12 is a cross-sectional view of the prosthesis of FIG. 9 along line 12—12.
Figure 13:
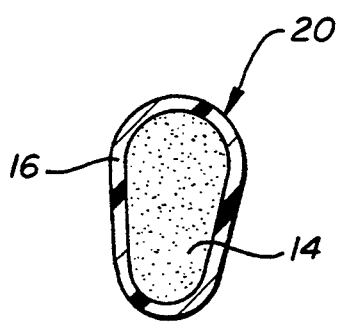
FIG. 13 is a cross-sectional view of the prosthesis of FIG. 9 along line 13—13.
Figure 14:
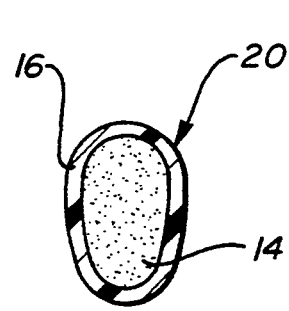
FIG. 14 is a cross-sectional view of the prosthesis of FIG. 9 along line 14—14.
Figure 15:
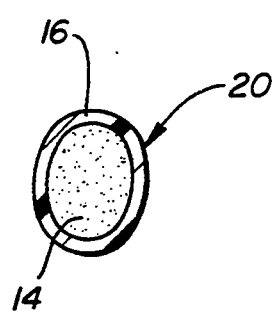
FIG. 15 is a cross-sectional view of the prosthesis of FIG. 9 along line 15—15.
Figure 16:
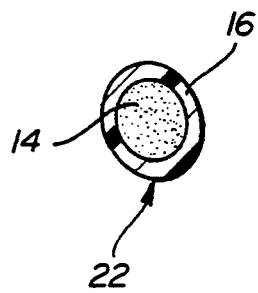
FIG. 16 is a cross-sectional view of the prosthesis of FIG. 9 along line 16—16.
Figure 17:
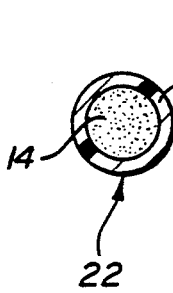
FIG. 17 is a cross-sectional view of the prosthesis of FIG. 9 along line 17—17.
Figure 18:
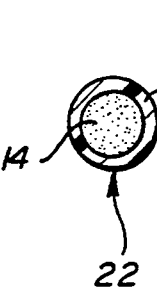
FIG. 18 is a cross-sectional view of the prosthesis of FIG. 9 along line 18—18.
Figure 19:
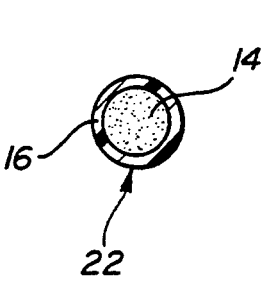
FIG. 19 is a cross-sectional view of the prosthesis of FIG. 9 along line 19—19.

Referring to FIGS. 9–19 there is shown prosthesis 10 in its final molded condition with various cross-sections taken therethrough showing the outer sheath and the inner core 14.

As stated above, the figures disclose a stem 9 or 10 in the form of a beam for a prosthesis such as a hip prosthesis, designed in a manner to better match the stiffness of the hip stem to the human femur or any other bone. This design is done by computer modeling the composite structure. The model uses a Transfer Index (TI) as a measure of how effectively the load is transferred in a physiological manner from prosthesis to bone wherein:

$$TI = \frac{\text{Cortical Bone Stress with Implant}}{\text{Cortical Bone Stress Intact Bone}}$$

A TI value of 1.0 indicates perfect transfer, no change from the physiological case. Deviation from 1 indicates a mismatch in load transfer.

The analysis also uses a Design Factor (DF) as a measure of how close the computed stress in the prosthesis is to its limiting value.

$$DF = \frac{\text{Strength of Implant}}{\text{Stress Induced in Implant}}$$

The design factor should be greater than 1.0.

In the preferred embodiment, the stem or beam structure consists of core 14 and outer wrap or sheath 16 constructed to combine the necessary strength and stiffness along the prosthesis.

This composite stem design dissipates loads quickly into bone in the proximal region 20, simulating the normal intact bone situation. Also the design permits the composite stem structure to be tailored to a specific bone geometry. Usually, this is accomplished by using an anatomical data base for determining the desired size and shape. That is, core 14 can be changed to achieve adequate stem bulk and the short fiber content. The outer sheath 16 wrap angles can also be changed to maintain desired rigidity and strength along the length of the stem.

Using a simplified beam model of bone and prosthesis, the initial requirements for prostheses rigidity and strength are established using two load inputs. The two load inputs involve the maximum load seen in the walking cycle and in rising from a chair. The model is then used to evaluate the many possible combinations of sheath fiber wrap orientation and sheath thickness until the desired Transfer Index, Design Factor and other properties are obtained. By observing transfer index patterns along the long axis of the stem, regions where rigidity changes are required can be identified. Rigidity is adjusted to Transfer Index near 1.0 by changing outer sheath wrap and/or the core short fiber volume ratio, while maintaining sufficient strength (Design Factor).

Once the outer sheath and core designs have been established by the simplified beam model, these designs are transferred to the commercially available ANSYS Finite Element Model for minor adjustments in wrap angle of the outer sheath and fine tuning of the stem stiffness or changing the short fiber volume ratio.

It has been found from analyzing the stiffness of human femurs that desired regional properties for a prosthetic hip stem are:

| Region | Modulus, psi |
| --- | --- |
| Stem Neck Region | $8.2 \times 10^6 \pm 10\%$ |
| Proximal Stem | $1.6 \times 10^6 \pm 10\%$ |
| Distal Stem | $1.1 \times 10^6 \pm 10\%$ |

In the preferred embodiment, stem modulus values are achieved by using a core of 30% short carbon fibers reinforced PEEK (such as Vitrex 450CA30 or 150CA30 from ICI) and by using the following carbon fiber reinforced PEEK sheath layers/outer wrap angles (with 0 being the longitudinal axial direction of the stem, (+) being clockwise and (−) being a helical counter clockwise wrap). In the trunion/neck region (area A3 of FIG. 6), one layer at +45 alternating with one layer at −45, covered by 6 sets of ±15 alternating layers, covered by one layer at −45 alternating with one at +45 for a total of 16 layers. In the proximal and distal stem area (A2 and A1 of FIGS. 5 and 6), two layers at +30 alternated with two layers at −30 covered by eight at 90°, covered by two layers at −30 alternating with two at +30 for a total of 16 layers. These layers are placed over the short fiber reinforcing PEEK core. Each layer is about 0.005″ thick.

This preferred construction of the stem is such that the outer sheath carbon fibers provide resistance to bending and torsion and carry the major portion of the stress while retaining the desired transfer index. By varying the orientation of the fibers of the outer wrap or the thickness in a particular region of the beam or stem, and/or the short fiber volume ratio of the core, the required contribution to rigidity and strength is achieved. The outer wrap is continuous from the distal region to the neck to enable a smooth transference of joint load applied to the neck to the outer wrap of the stem. The core and the sheath each have a predetermined stiffness as defined by a modulus of elasticity wherein the core has a lower modulus than the sheath. The modulus of elasticity of the core varies from 0.5 to $2.8 \times 10^6$ psi and the modulus of the sheath varies from 1.5 to $10 \times 10^6$ psi.

In the preferred method of manufacture, core 14 is injection molded molten PEEK reinforced with short carbon fiber generally oriented parallel to the longitudinal axis. The core blank is the actual core of the prosthesis, but extended in length at both ends to provide for later support in processing machines. The molding process forms the approximately 45° medial-lateral (M-L) bend in the case of a hip stem so that the longitudinal axis of the stem is curved in the M-L plane.

As shown in FIGS. 5-8, after solidification, the short carbon fiber/PEEK core is then covered with a sheath of carbon fiber reinforced preimpregnated filament as discussed above. This may be accomplished either by wrapping the core with carbon/PEEK commingled yarn to form a series of layers or by wrapping with carbon fiber reinforced preimpregnated tape (approximately ⅛″ wide). Such a material may be in the form of preimpregnated ribbon or filament wound on a spool. The filament or tape is wound along the length of the core to form layers at the predetermined angular orientations, which may vary from layer to layer and/or within each layer. For example, a single sheath layer is a layer having fibers oriented at 30° to the longitudinal axis in the distal stem area 22, 30° in the proximal stem area 20 and 45° in the neck area 18 with transition areas at varying angles between the distal stem, proximal stem and neck areas.

It should be noted that several layers contain wraps perpendicular to the central longitudinal axis ($\Theta = 90°$) wound around the prosthesis core. Since, for a hip prosthesis, the longitudinal axis includes a 35°-55° bend in the plane parallel to the medial-lateral plane of the body, the filament fibers in these layers are not parallel to one another even though they are all perpendicular to the axis of the core.

A strip/filament winding machine suitable for varying the angle of the filament with respect to the longitudinal axis of the core filler within a single layer or pass is disclosed in U.S. Pat. No. 4,750,960, the teachings of which are incorporated herein. Such a machine may be obtained from Automated Dynamics Corporation (ADC) in Schenectedy, New York. The machine winds the core with any number of layers of mono-filament or tape with the reinforcing fibers oriented in any desired pattern such as that described above herein.

Once the core has been covered with the predetermined number of layers of preimpregnated filament or tape, the composite is placed in a final mold which conforms to the desired final shape. The material is heated to a temperature sufficient to cause the thermoplastic in the outer sheath to soften and then the composite structure is allowed to consolidate under pressure. If desired, the mold may include a roughened surface to impart such a surface to the outer surface of the prosthesis, such as for fixation enhancement by tissue ingrowth. Alternatively, the method taught in U.S. Pat. No. 4,778,469, owned by the assignee of the present invention, may be used to form an attachment surface on the outside of the composite stem.

While several examples of the present invention have been described, it is obvious that many changes and modifications may be made thereunto, without departing from the spirit and scope of the invention.

We claim:

1. A beam of predetermined length adapted for implantation within a bone to support a load capable of applying bending and torsional loading forces, consisting essentially of:
   an injection molded elongated core formed of short filament fibers having a length of less than four millimeters embedded in a thermoplastic polymer, said short filament fibers generally oriented parallel to a longitudinal axis of the core; and
   encasing the core, a sheath formed of a plurality of elongated carbon filament fibers embedded in a thermoplastic polymer, each fiber individually helically wound around the core to form a layer so that a plurality of layers are formed and molded thereto, wherein the sheath and the core each have a stiffness as defined by a modulus of elasticity wherein the core has a lower modulus than the sheath.

2. The beam as set forth in claim 1 wherein the filament fibers in said sheath are carbon fibers impregnated with a thermoplastic resin.

3. The beam as set forth in claim 2 wherein said thermoplastic resin is polyetheretherketone.

4. The beam as set forth in claim 1 wherein said sheath filament fibers are wound around said core at angles with respect to said longitudinal axis of said core which vary along said axis of said core to ensure adequate bending and torsional strength in regions of the beam subjected to high stress.

5. The beam as set forth in claim 4 wherein said sheath filament fibers are wound around said core at angles with respect to said longitudinal axis of said core which vary along said axis of said beam to produce a modulus of elasticity of the beam which varies along the length thereof.

6. The beam as set forth in claim 1 wherein the modulus of elasticity of the core varies from $0.5-2.8 \times 10^6$ psi and the modulus of the sheath varies from $1.5-10 \times 10^6$ psi.

7. The beam as set forth in claim 1 wherein the sheath is comprised of a plurality of discrete layers of said fibers, each oriented at predetermined angles with respect to the longitudinal axis of the beam to produce a beam having a stiffness at any point therealong generally corresponding to the stiffness of the bone adjacent the beam after implantation of the beam.

8. The beam as set forth in claim 7 wherein the angular orientation of said wound fibers varies within each discrete layer.

9. A beam of predetermined length adapted for implantation within a femur of quantifiable stiffness along the length thereof, said beam in the form of an implant having a neck region, a proximal stem region and a distal stent region, consisting essentially of;
   an injection molded core having a longitudinal axis and formed of short filament fibers embedded in a thermoplastic polymer, said fibers generally oriented parallel to a longitudinal axis of said core:
   a sheath formed of elongated filament fibers embedded in a thermoplastic polymer helically wound around the core in discrete layers with each layer consisting of a single fiber and molded thereto, wherein the sheath and the core each have a stiffness as defined by a modulus of elasticity wherein the core has a lower modulus than the sheath.

10. The beam as set forth in claim 9 wherein the sheath is comprised of a plurality of discrete layers of said fibers oriented at various angles with respect to the longitudinal axis of the core to produce a beam having a stiffness at any point therealong, generally corresponding to the stiffness of the femur adjacent the beam after the implantation thereof within the femur.

11. The beam as set forth in claim 10 wherein said thermoplastic polymer is polyetheretherketone.

12. A complete prosthetic hip stem of predetermined length and shape for implantation into a femur having a quantifiable stiffness along the length thereof consisting essentially of:
   a core having a longitudinal axis and molded from polyetheretherketone containing chopped carbon fibers, said fibers generally oriented parallel to a longitudinal axis of said core;
   a sheath formed of elongated carbon fibers embedded in polyetheretherketone helically wound around the core and molded thereto, said sheath comprising a plurality of discrete layers, each layer formed a continuous length of said fibers, each oriented at predetermined angles with respect to the longitudinal axis of the core to produce a stem having a stiffness at any point therealong generally corresponding to the stiffness of the femur adjacent the stem after implantation of the stem, said core and said sheath forming said predetermined shape; and
   a trunion formed at a proximal end of said sheath, wherein the sheath and the core each have a stiffness as defined by a modulus of elasticity wherein the core has a lower modulus than the sheath.

13. The hip stem as set forth in claim 12 wherein the angular orientation of said wound fibers varies within each discrete layer.

14. The hip stem as set forth in claim 12 wherein said sheath filament fibers are wound around said core at angles with respect to said longitudinal axis of said core which vary along said axis of said core to ensure adequate bending and torsional strength in regions of the stem subjected to high stress.

15. The hip stem as set forth in claim 12 wherein the modulus of elasticity of the core is between 0.5 and $2.8 \times 10^6$ psi and the modulus of the sheath varies from $1.5-10 \times 10^6$ psi.

* * * * *